(12) United States Patent
Jolidon et al.

(10) Patent No.: US 6,399,641 B1
(45) Date of Patent: Jun. 4, 2002

(54) 2H-TETRAZOLE-AMIDE COMPOUNDS WITH THERAPEUTIC ACTIVITY AS METABOTROPIC GLUTAMATE RECEPTOR AGONISTS

(75) Inventors: Synese Jolidon, Blauen (CH); Vincent Mutel, Mulhouse (FR); Eric Vieira, Allschwil (CH); Juergen Wichmann, Steinen (DE)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 09/892,994

(22) Filed: Jun. 27, 2001

(30) Foreign Application Priority Data

Jul. 13, 2000 (EP) .............................................. 00115170

(51) Int. Cl.$^7$ ......................... A61K 31/41; A61P 25/00; C07D 257/08
(52) U.S. Cl. ..................... 514/382; 514/381; 548/251
(58) Field of Search .......................... 548/251; 514/381, 514/382

(56) References Cited

U.S. PATENT DOCUMENTS 5,266,578 A  *  11/1993  Raddatz et al. ............. 514/312

OTHER PUBLICATIONS

E. J. Schlager and K. Christensen, Cytotechnology, vol. 30, pp. 71–83 (1999).

* cited by examiner

Primary Examiner—Robert W. Ramsuer
Assistant Examiner—Andrea D. Small
(74) Attorney, Agent, or Firm—George W. Johnston; Patricia S. Rocha-Tramaloni; Arthur D. Dawson

(57) ABSTRACT

The present invention is a series of 2H-tetrazole-5-yl-amide derivatives showing activity as ligands of metabotropic glutamate receptors.

49 Claims, No Drawings

2H-TETRAZOLE-AMIDE COMPOUNDS WITH THERAPEUTIC ACTIVITY AS METABOTROPIC GLUTAMATE RECEPTOR AGONISTS

FIELD OF INVENTION

The present invention is generally related to novel 2H-tetrazole-5-yl amide compounds, a process for making the compounds, a medicament incorporating the compounds and a method of treatment utilizing the compounds as metabotropic glutamate receptor agonists.

BACKGROUND

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors. At present, eight different members of these mGluRs' are known and of these some even have sub-types. On the basis of structural parameters, the different second messenger signalling pathways and the different affinity to low-molecular weight chemical compounds, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain. Other treatable indications by administration of agonists of metabotropic gluamate receptors include restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression.

SUMMARY

The present invention is includes 2H-tetrazole-5-yl-amide derivatives of the formula

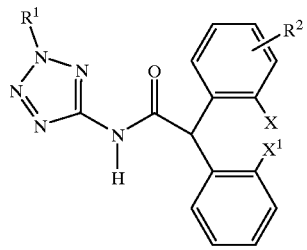

wherein
- $R^1$ is hydrogen, lower alkyl, —$(CH_2)_n$—$CF_3$, —$(CH_2)_n$—$CHF_2$, —$(CH_2)_n$—CN, —$(CH_2)_n$-cycloalkyl, —$(CH_2)_n$—O-lower alkyl, —$(CH_2)_n$—O-cycloalkyl or —$(CH_2)_n$—C(O)O-lower alkyl;
- $R^2$ is hydrogen, lower alkyl, lower alkoxy, halogen, —C(O)-lower alkyl, —C(O)OH, —C(O)O-lower alkyl, —$NR^3R^4$ or —C(O)—$NR^3R^4$ and wherein $R^3$ and $R^4$ are hydrogen or lower alkyl;
- X and X' are taken together to form —O—, —S—, —$CH_2$, —$OCH_2$—, a bridge between the two rings or individually are two hydrogen atoms not capable of forming a bridge between the two rings; and
- n signifies 0, 1, 2, 3 or 4;
- or a pharmaceutically acceptable salt thereof.

A compound of structure I and a pharmaceutically acceptable salt thereof are novel and are distinguished by valuable therapeutic properties.

It has been surprisingly found that the compounds of formula I are group 1 metabotropic glutamate receptor agonists (mGluR).

DETAILED DESCRIPTION

A preferred compound of formula 1 has the structure formula 1A

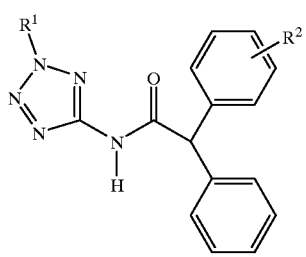

Preferred compounds having structure 1A include compounds having $R^1$ being lower alkyl, —$(CH_2)_n$—C(O)O-lower alkyl, —$(CH_2)_n$-cycloalkyl, —$(CH_2)_n$—O-lower alkyl, —$(CH_2)_n$—$CF_3$, —$(CH_2)_n$—$CHF_2$, or —$(CH_2)_n$—CN and $R^2$ being hydrogen.

The following are examples of preferred compounds having the structure of formula 1A:
N-(2-methyl-2H-tetrazol-5-yl)-2,2-diphenyl-acetamide,
N-(2-ethyl-2H-tetrazol-5-yl)-2,2-diphenyl-acetamide,
N-(2-cyclopropylmethyl-2H-tetrazol-5-yl)-2,2-diphenyl-acetamide,
N-(2-isopropyl-2H-tetrazol-5-yl)-2,2-diphenyl-acetamide,
2,2-diphenyl-N-[2-(2,2,2-trifluoro-ethyl)-2H-tetrazol-5-yl]-acetamide,
2,2-diphenyl-N-(2-propyl-2H-tetrazol-5-yl)-acetamide,
N-(2-methoxymethyl-2H-tetrazol-5-yl)-2,2-diphenyl-acetamide, N-(2-tert-butyl-2H-tetrazol-5-yl)-2,2-diphenyl-acetamide,
N-(2-difluoromethyl-2H-tetrazol-5-yl)-2,2-diphenyl-acetamide,
N-(2-cyanomethyl-2H-tetrazol-5-yl)-2,2-diphenyl-acetamide and
(5-diphenylacetylamino-tetrazol-2-yl)-acetic acid methyl ester.

Another preferred compound of formula 1 has the structure 1B

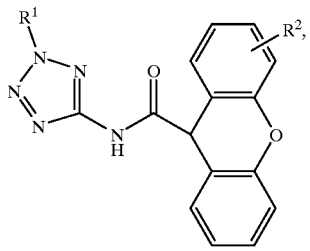

IB wherein X and X' are joined together as —O— thereby forming a bridge between the rings.

Preferred compounds having structure 1B include compounds having R¹ being lower alkyl, —(CH₂)ₙ-cycloalkyl, —(CH₂)ₙ—CF₃, —(CH₂)ₙ—CHF₂, —(CH₂)ₙ—CN, —(CH₂)ₙ—C(O)O-lower alkyl or —(CH₂)ₙ—O-lower alkyl and R² being hydrogen and R¹ being lower alkyl and R² being lower alkoxy.

The following are examples of preferred compounds having the structure 1B:

9H-xanthene-9-carboxylic acid (2-methyl-2H-tetrazol-5-yl)-amide,
9H-xanthene-9-carboxylic acid (2-ethyl-2H-tetrazol-5-yl)-amide,
9H-xanthene-9-carboxylic acid (2-cyclopropylmethyl-2H-tetrazol-5-yl)-amide,
9H-xanthene-9-carboxylic acid (2-isopropyl-2H-tetrazol-5-yl)-amide,
9H-xanthene-9-carboxylic acid [2-(2,2,2-trifluoro-ethyl)-2H-tetrazol-5-yl]-amide,
9H-xanthene-9-carboxylic acid (2-propyl-2H-tetrazol-5-yl)-amide,
9H-xanthene-9-carboxylic acid (2-methoxymethyl-2H-tetrazol-5-yl)-amide,
9H-xanthene-9-carboxylic acid (2-tert-butyl-2H-tetrazol-5-yl)-amide,
9H-xanthene-9-carboxylic acid (2-difluoromethyl-2H-tetrazol-5-yl)-amide,
9H-xanthene-9-carboxylic acid (2-cyanomethyl-2H-tetrazol-5-yl)-amide,
{5-[(9H-xanthene-9-carbonyl)-amino]-tetrazol-2-yl}-acetic acid methyl ester,
(RS)-1-methoxy-9H-xanthene-9-carboxylic acid (2-ethyl-2H-tetrazol-5-yl)-amide,
(RS)-2-methoxy-9H-xanthene-9-carboxylic acid (2-ethyl-2H-tetrazol-5-yl)-amide and
(RS)-4-Methoxy-9H-xanthene-9-carboxylic acid (2-ethyl-2H-tetrazol-5-yl)-amide Another preferred compound from formula 1 is a compound with the structure of formula 1C.

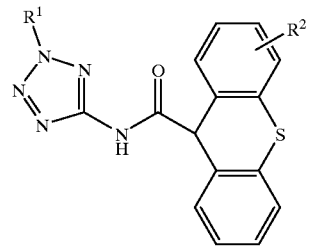

IC wherein X and X' are joined together as —S—, thereby forming a bridge between the rings. A preferred example of the compound of formula 1C is 9H-thioxanthene-9-carboxylic acid (2-ethyl-2H-tetrazol-5-yl)-amide.

Yet another preferred compound of formula 1 has the structure 1D.

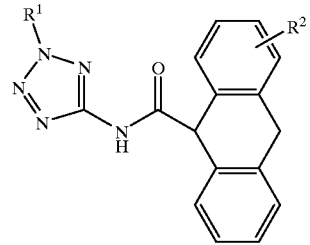

ID wherein X and X' are joined together as —CH₂—, thereby forming a bridge between the rings. A preferred example of a compound with the structure of formula 1D is 9,10-dihydro-anthracene-9-carboxylic acid (2-ethyl-2H-tetrazol-5-yl)-amide.

Another preferred compound of formula I has the structure IE

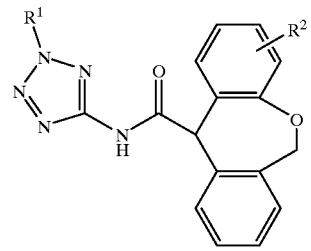

IE wherein X and X' are joined together as —OCH₂—, thereby forming a bridge between the rings; and wherein R¹ and R² are as defined in formula I above. A preferred compound of formula 1E is (RS)-6,11-dihydro-dibenzo [b,e]oxepine-11-carboxylic acid (2-ethyl-2H-tetrazol-5-yl)-amide.

Also preferred are compounds of the present invention of formula IA, IB, IC, ID and IE, wherein R² is hydrogen.

The compound of the invention embraces all stereoisomeric forms of formula I in addition to the racemates.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkoxy" denotes a lower alkyl residue in the sense of the foregoing definition bonded via an oxygen atom.

The term "cycloalkyl" embraces cyclic alkyl rings having between 3 to 7 carbon atoms.

The compounds of formula I and their pharmaceutically acceptable salts can be manufactured by processes, which comprises

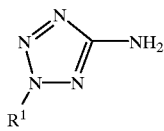

II with a compound of formula

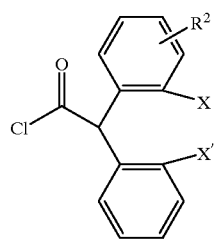

III to a compound of formula

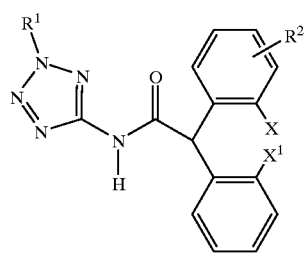

I wherein the substituents are as designated above and, if desired, converting a functional group in a compound of formula I into another functional group and, if desired, converting a compound of formula I into a pharmaceutically acceptable salt.

In accordance with process variant described above to a stirred solution of a compound of formula II, for example of 5-amino-2-methyl-2H-tetrazole, 5-amino-2-ethyl-2H-tetrazole or 5-amino-2-cyclopropylmethyl-2H-tetrazole in dichloromethane in the presence of pyridine and DMAP (2,2-bis(hydroxymethyl)propionic acid) the corresponding compound of formula III, for example diphenylacetyl chloride or 9H-xanthene-9-carbonyl chloride is added. The reaction is carried out at about 0° C.

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

Scheme 1 gives an overview of the manufacture of the compounds of formula I. The manufacture of representative compounds of formula I is described in detail in examples 1–28. The starting material is known or may be prepared by known methods. The compounds of formula I may be prepared in conventional manner by methods, known in the art.

Scheme 1

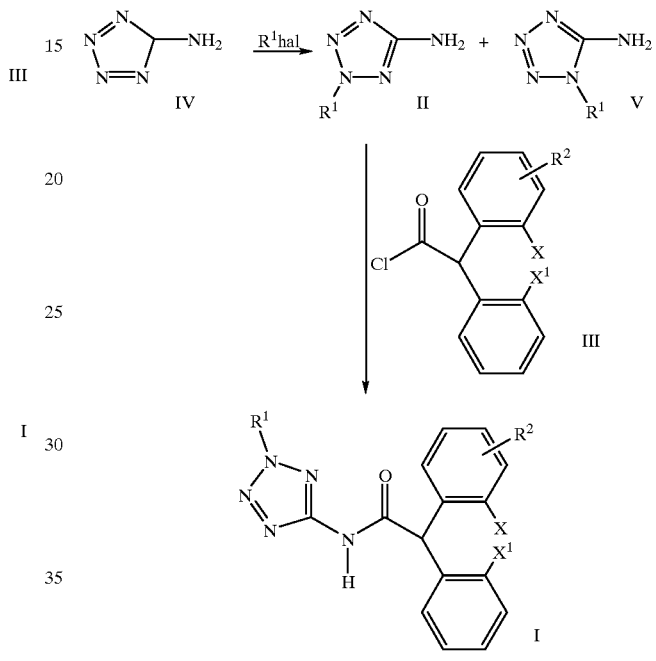

The substituents are as designated above.

The compounds of formula I and their pharmaceutically acceptable salts are, as already mentioned above, metabotropic glutamate receptor agonists and can be used for the treatment or prevention of acute and/or chronic neurological disorders responsive to modulation of the metabotropic glutamate receptor, such as psychosis, schizophrenia, Alzheimer's disease, cognitive disorders and memory deficits, as well as acute and chronic pain.

Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

It has been shown that the compounds of the invention show agonistic activities, as measured in the assay described below, of 10 $\mu$M or less, typically 1 $\mu$M or less, and ideally of 0.3 $\mu$M or less.

Examples of such compounds are

| EC$_{50}$ ($\mu$M) | Example No. |
|---|---|
| 0.220 | 1 |
| 0.180 | 2 |
| 0.100 | 7 |
| 0.045 | 8 |
| 2.000 | 9 |
| 0.170 | 10 |
| 0.470 | 24 |
| 1.390 | 25 |
| 0.190 | 27 |

TEST METHOD cDNA encoding for rat mGlu1a receptor obtained from Prof. S. Nakanishi (Kyoto, Japan) was transiently transfected into EBNA cells using a procedure described by Schlaeger & Christensen, 1998. [Ca$^{2+}$]i measurement were performed on mGlu1a transfected EBNA cells after incubation of the cells with Fluo-3 AM (0.5 $\mu$M final concentration) for 1 hour at 37° C. followed by 4 washes with assay buffer (DMEM supplemented with Hank's salt and 20 mM HEPES). [Ca$^{2+}$]i measurement were done using a fluorometric imaging plate reader (FLIPR, Molecular Devices Corporation, La Jolla, Calif., USA). When compounds were evaluated as antagonists they were tested against 10 $\mu$M glutamate as agonist.

The inhibition (antagonists) or activation (agonists) curves were fitted with a four parameter logistic equation giving EC$_{50}$, IC$_{50}$ and Hill coefficient using the iterative non linear curve fitting software Origin (Microcal Software Inc., Northampton, Mass., USA). E.-J. Schlaeger and K. Christensen Transient gene expression in mammalian cells grown in serum-free suspension culture. Cytotechnology, 30:71–83, 1999.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, the use of compounds of formula I and of pharmaceutically acceptable salts thereof for the production of medicaments, especially for the control or prevention of acute and/or chronic neurological disorders of the aforementioned kind, is also an object of the invention.

EXAMPLE 1

N-(2-Methyl-2H-tetrazol-5-yl)-2,2-diphenyl-acetamide

To a stirred solution of 5-amino-2-methyl-2H-tetrazole (0.50 g, 5.05 mmol), pyridine (0.48 g, 6.06 mmol) and DMAP (0.06 g, 0.51 mmol) in dichloromethane (30 ml) was added at 0° C. diphenylacetyl chloride (1.16 g, 5.05 mmol). Stirring was continued at RT for 2 h, the reaction mixture was poured into sat. NaHCO$_3$ solution (50 ml) and extracted with dichloromethane (3×50 ml). The combined organic layers were washed with brine (70 ml), dried (Na$_2$SO$_4$) and evaporated. The crude product was crystallized from ethyl acetate/hexane to give the title compound (0.83 g, 56%) as a white solid, m.p. 218° C. (dec.) and MS: m/e=293.1 (M+H$^+$).

EXAMPLE 2

9-Xanthene-9-carboxylic acid (2-methyl-2H-tetrazol-5-yl)-amide

The title compound, white solid, m.p. 247° C. (dec.) and MS: m/e=307.1 (M$^+$) was prepared in accordance with the general method of example 1 from 5-amino-2-methyl-2H-tetrazole and 9H-xanthene-9-carbonyl chloride.

EXAMPLE 3

N-(2-Ethyl-2H-tetrazol-5-yl)-2,2-diphenyl-acetamide

The title compound, white solid, m.p. 169–170° and MS: (neg. ions): m/e=306.2 (M$^+$–H) was prepared in accordance with the general method of example 1 from 5-amino-2-ethyl-2H-tetrazole and diphenylacetyl chloride.

EXAMPLE 4

9H-Xanthene-9-carboxylic acid (2-ethyl-2H-tetrazol-5-yl)-amide

The title compound, white solid, m.p. 228° C. (dec.) and MS: (neg. ions): m/e=320.0 (M$^+$–H) was prepared in accordance with the general method of example 1 from 5-amino-2-ethyl-2H-tetrazole and 9H-xanthene-9-carbonyl chloride.

EXAMPLE 5

N-(2-Cyclopropylmethyl-2H-tetrazol-5-yl)-2,2-diphenyl-acetamide

The title compound, white solid, m.p. 147–148° and MS: m/e=334.3 (M$^+$+H) was prepared in accordance with the general method of example 1 from 5-amino-2-cyclopropylmethyl-2H-tetrazole and diphenylacetyl chloride.

EXAMPLE 6

9H-Xanthene-9-carboxylic acid (2-cyclopropylmethyl-2H-tetrazol-5-yl)-amide

The title compound, white solid, m.p. 222–224° C. and MS: (neg. ions): m/e=346.2 (M$^+$−H) was prepared in accordance with the general method of example 1 from 5-amino-2-cyclopropylmethyl-2H-tetrazole and 9H-xanthene-9-carbonyl chloride.

EXAMPLE 7

N-(2-Isopropyl-2H-tetrazol-5-yl)-2,2-diphenyl-acetamide

The title compound, white solid, m.p. 175–177° and MS: (neg. ions): m/e=320.2 (M+−H) was prepared in accordance with the general method of example 1 from 5-amino-2-isopropyl-2H-tetrazole and diphenylacetyl chloride.

EXAMPLE 8

9H-Xanthene-9-carboxylic acid (2-isopropyl-2H-tetrazol-5-yl)-amide

The title compound, white solid, MS: (neg. ions): m/e=334.2 (M+−H) was prepared in accordance with the general method of example 1 from 5-amino-2-isopropyl-2H-tetrazole and 9H-xanthene-9-carbonyl chloride.

EXAMPLE 9

2,2-Diphenyl-N-[2-(2,2,2-trifluoro-ethyl)-2H-tetrazol-5-yl]-acetamide

The title compound, white solid, m.p. 146–148 and MS: (neg. ions): m/e=360.0 (M+−H) was prepared in accordance with the general method of example 1 from 5-amino-$^2$-(2,2,2-trifluoroethyl)-2H-tetrazole and diphenylacetyl chloride.

EXAMPLE 10

9H-Xanthene-9-carboxylic acid [2-(2,2,2-trifluoro-ethyl)-2H-tetrazol-5-yl]-amide The title compound, white solid, m.p. 209–210 and MS: (neg. ions): m/e=374.1 (M+−H) was prepared in accordance with the general method of example 1 from 5-amino-2-(2,2,2-trifluoroethyl)-2H-tetrazole and 9H-xanthene-9-carbonyl chloride.

EXAMPLE 11

2,2-Diphenyl-N-(2-propyl-2H-tetrazol-5-yl)-acetamide

The title compound, white solid, m.p. 124–125° and MS: (neg. ions): m/e=320.0 (M+−H) was prepared in accordance with the general method of example 1 from 5-amino-2-propyl-2H-tetrazole and diphenylacetyl chloride.

EXAMPLE 12

9H-Xanthene-9-carboxylic acid (2-propyl-2H-tetrazol-5-yl)-amide

The title compound, white solid,, m.p. 208–209° and MS: (neg. ions): m/e=334.1 (M+−H) was prepared in accordance with the general method of example 1 from 5-amino-2-propyl-2H-tetrazole and 9H-xanthene-9-carbonyl chloride.

EXAMPLE 13

N-(2-Methoxymethyl-2H-tetrazol-5-yl)-2,2-diphenyl-acetamide

The title compound, white solid, m.p. 127–128° and MS: (neg. ions): m/e=322.2 (M+−H) was prepared in accordance with the general method of example 1 from 5-amino-2-methoxymethyl-2H-tetrazole and diphenylacetyl chloride.

EXAMPLE 14

9H-Xanthene-9-carboxylic acid (2-methoxymethyl-2H-tetrazol-5-yl)-amide

The title compound, white solid, m.p. 221–222 and MS: (neg. ions): m/e=336.1 (M+−H) was prepared in accordance with the general method of example 1 from 5-amino-2-methoxymethyl-2H-tetrazole and 9H-xanthene-9-carbonyl chloride.

EXAMPLE 15

N-(2-tert-Butyl-2H-tetrazol-5-yl)-2,2-diphenyl-acetamide

The title compound, white solid, m.p. 191–192° and MS: (neg. ions): m/e=334.3 (M+−H) was prepared in accordance with the general method of example 1 from 5-amino-2-tert-butyl-2H-tetrazole and diphenylacetyl chloride.

EXAMPLE 16

9H-Xanthene-9-carboxylic acid (2-tert-butyl-2H-tetrazol-5-yl)-amide

The title compound, white solid, m.p. 230–231° and MS: (neg. ions): m/e=348.2 (M+−H) was prepared in accordance with the general method of example 1 from 5-amino-2-tert-butyl-2H-tetrazole and 9H-xanthene-9-carbonyl chloride.

EXAMPLE 17

N-(2-Difluoromethyl-2H-tetrazol-5-yl)-2,2-diphenyl-acetamide

The title compound, white solid, m.p. 143–145° and MS: (neg. ions): m/e=328.1 (M+−H) was prepared in accordance with the general method of example 1 from 5-amino-2-difluoromethyl-2H-tetrazole and diphenylacetyl chloride.

EXAMPLE 18

9H-Xanthene-9-carboxylic acid (2-difluoromethyl-2H-tetrazol-5-yl)-amide

The title compound, white solid, m.p. 168–169° and MS: (neg. ions): m/e=342.0 (M+−H) was prepared in accordance with the general method of example 1 from 5-amino-2-difluoromethyl-2H-tetrazole and 9H-xanthene-9-carbonyl chloride.

EXAMPLE 19

N-(2-Cyanomethyl-2H-tetrazol-5-yl)-2,2-diphenyl-acetamide

The title compound, white solid, m.p. 173–174° and MS: m/e=319.3 (M++H) was prepared in accordance with the general method of example 1 from (5-amino-tetrazol-2-yl)-acetonitrile and diphenylacetyl chloride.

EXAMPLE 20

9H-Xanthene-9-carboxylic acid (2-cyanomethyl-2H-tetrazol-5-yl)-amide

The title compound, white solid, m.p. 204–205° and MS: m/e=333.2 (M++H) was prepared in accordance with the general method of example 1 from (5-amino-tetrazol-2-yl)-acetonitrile and 9H-xanthene-9-carbonyl chloride.

EXAMPLE 21

(5-Diphenylacetylamino-tetrazol-2-yl)-acetic acid methyl ester

The title compound, white solid, m.p. 168–169° and MS: (neg. ions): m/e=350.2 (M+–H) was prepared in accordance with the general method of example 1 from (5-amino-tetrazol-2-yl)-acetic acid methyl ester and diphenylacetyl chloride.

EXAMPLE 22

{5-[(9H-Xanthene-9-carbonyl)-amino]-tetrazol-2-yl}-acetic acid methyl ester

The title compound, white solid, m.p. 243–244° and MS: (neg. ions): m/e=364.0 (M+–H) was prepared in accordance with the general method of example 1 from (5-amino-tetrazol-2-yl)-acetic acid methyl ester and 9H-xanthene-9-carbonyl chloride.

EXAMPLE 23

9,10-Dihydro-anthracene-9-carboxylic acid (2-ethyl-2H-tetrazol-5-yl)-amide

The title compound, white solid, m.p. 206–207° and MS: (neg. ions): m/e=318.3 (M+–H) was prepared in accordance with the general method of example 1 from 5-amino-2-ethyl-2H-tetrazole and 9,10-dihydro-anthracene-9-carbonyl chloride.

EXAMPLE 24

(RS)-6,11-Dihydro-dibenzo[b,e]oxepine-11-carboxylic acid (2-ethyl-2H-tetrazol-5-yl)-amide The title compound, yellow solid, m.p. 158–159° and MS: (neg. ions): m/e=334.1 (M+–H) was prepared in accordance with the general method of example 1 from 5-amino-2-ethyl-2H-tetrazole and 6,11-dihydro-dibenzo[b,e]oxepine-11-carbonyl chloride.

EXAMPLE 25

9H-Thioxanthene-9-carboxylic acid (2-ethyl-2H-tetrazol-5-yl)-amide

The title compound, white solid, m.p. 228° C. (dec.) and MS: (neg. ions): m/e=320.0 (M+–H) was prepared in accordance with the general method of example 1 from 5-amino-2-ethyl-2H-tetrazole and 9H-xanthene-9-carbonyl chloride.

EXAMPLE 26

(RS)-1-Methoxy-9H-xanthene-9-carboxylic acid (2-ethyl-2H-tetrazol-5-yl)-amide

The title compound, white solid, m.p. 259–260° C. (dec.) and MS: (pos. ions): m/e=352.3 (M++H) was prepared in accordance with the general method of example 1 from 5-amino-2-ethyl-2H-tetrazole and (RS)-1-methoxy-9H-xanthene-9-carbonyl chloride.

EXAMPLE 27

(RS)-2-Methoxy-9H-xanthene-9-carboxylic acid (2-ethyl-2H-tetrazol-5-yl)-amide

The title compound, white solid, m.p. 208–210° C. (dec.) and MS: (pos. ions): m/e=352.3 (M++H) was prepared in accordance with the general method of example 1 from 5-amino-2-ethyl-2H-tetrazole and (RS)-2-methoxy-9H-xanthene-9-carbonyl chloride.

EXAMPLE 28

(RS)-4-Methoxy-9H-xanthene-9-carboxylic acid (2-ethyl-2H-tetrazol-5-yl)-amide

The title compound, white solid, m.p. 239–240° C. (dec.) and MS: (pos. ions): m/e=352.3 (M++H) was prepared in accordance with the general method of example 1 from 5-amino-2-ethyl-2H-tetrazole and (RS)-4-methoxy-9H-xanthene-9-carbonyl chloride.

Preparation of 2-substituted 5-amino-2H-tetrazoles

5-Amino-2-methyl-2H-tetrazole is obtained from 5-aminotetrazole-monohydrate and methyl iodide by the method of R. A. Henri et al., J.Amer.Chem.Soc. 76, 923 (1954).

5-Amino-2-ethyl-2H-tetrazole is prepared according to the method of R. N. Butler et al., J.Chem.Res.Synopsis 1988, 188.

5-amino-2-cyclopropylmethyl-2H-tetrazole (amorphous white solid and MS: m/e=139.1 (M+)) is similarly obtained from 5-aminotetrazole-monohydrate and cyclopropylmethyl iodide using the general method of R. N. Butler et al. (loc. cit.).

5-Amino-2-propyl-2H-tetrazole (liquid; MS: m/e=127.1 (M+)) is similarly obtained from 5-aminotetrazole-monohydrate and propyl iodide using the general method of R. N. Butler et al. (loc. cit.).

5-Amino-2-isopropyl-2H-tetrazole (liquid, MS: m/e=127.1 (M+)) is similarly obtained from 5-aminotetrazole-monohydrate and isopropyl iodide using the general method of R. N. Butler et al. (loc. cit.).

5-Amino-2-tert-butyl-2H-tetrazole (white solid; m.p.=114–115°) is obtained from 5-aminotetrazole-monohydrate and O-tert-butyl-N,N'-dicyclohexylisourea, according to the general method described by R. A. Henry et al., J.Heterocycl.Chem. 13, 391 (1976).

5-Amino-2-cyclopropylmethyl-2H-tetrazole (amorphous white solid and MS: m/e=139.1 (M+)) is similarly obtained from 5-aminotetrazole-monohydrate and cyclopropylmethyl iodide using the general method of R. N. Butler et al. (loc. cit.).

5-Amino-2-(2,2,2-trifluoroethyl)-2H-tetrazole (white solid; m.p.=95–97°) is obtained from 5-aminotetrazole-monohydrate and 2,2,2-trifluoroethyl trifluoromethanesulfonate, in analogy to W. G. Reifenrath et al., J.Med.Chem. 23, 985 (1980).

5-Amino-2-methoxymethyl-2H-tetrazole (waxy solid; MS: m/e=129.0 (M+)) is obtained from 5-aminotetrazolemonohydrate and chloromethyl methyl ether using the general method of R. N. Butler et al. (loc. cit.).

5-Amino-2-difluoromethyl-2H-tetrazole (liquid; MS: m/e=136.0 (M++H)) is obtained from 5-aminotetrazole-monohydrate and chlorodifluormethane, in analogy to the method described by V. G. Poludnenko et al., Chem.Heterocycl.Comp. (Engl.Transl.) 20, 422 (1984).

(5-Amino-tetrazol-2-yl)-acetonitrile (white solid; m.p.= 105–106°) is obtained from 5-aminotetrazole-monohydrate and chloroacetonitrile, according to the method described by S. R. Buzilova et al., J.Org.Chem. USSR (Engl.Transl.) 25, 1375 (1989).(5-Amino-tetrazol-2-yl)-acetic acid methyl ester (white solid; m.p.=127–128°) is obtained from 5-aminotetrazole-monohydrate and methyl bromoacetate, in analogy to the method described by S. R. Buzilova et al. (loc.cit.).

Preparation of the Carbonyl Chlorides 9,10-Dihydro-anthracene-9-carbonyl chloride was obtained by the method described in May & Mosettig, J.Amer.Chem.Soc.; 70; 688, (1948).

6,11-Dihydro-dibenzo[b,e]oxepine-11-carbonyl chloride (waxy solid) was obtained by the method described in Kumazawa et al., J.Med.Chem. 37, 804 (1994).

(RS)-4-Methoxy-9H-xanthene-9-carbonyl chloride was prepared according to general methods described in WO 9706178. 4-Methoxy-xanthene [J.Med.Chem., 32(10), 2357 (1989)] was deprotonated with lithium diisopropylamide in tetrahydrofuran followed by treatment with carbon dioxide. The resulting (RS)-4-methoxy-9H-xanthene-9-carboxylic acid (white solid and MS: m/e=256.0 (M+)) was chlorinated with oxalyl chloride in toluene/DMF and yielded after evaporation of the reagent and solvents, the crude acid chloride, which was directly used without further purification.

(RS)-1-Methoxy-9H-xanthene-9-carbonyl chloride was similarly obtained by chlorination of (RS)-1-methoxy-9H-xanthene-9-carboxylic acid (white solid and MS: m/e=257.1 (M++H) obtained from 1-methoxy-xanthene [J.Org.Chem., 22, 1644(1957)]).

(RS)-2-Methoxy-9H-xanthene-9-carbonyl chloride was similarly obtained by chlorination of (RS)-2-methoxy-9H-xanthene-9-carboxylic acid (white solid and MS: m/e=256.0 (M+) obtained from 2-methoxy-xanthene [J.Chem.Soc., 812 (1956)].

Example A

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example B

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example C

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compound of the formula

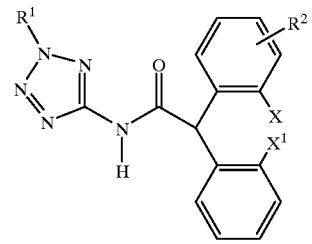

wherein $R^1$ is hydrogen, lower alkyl, —$(CH_2)_n$—$CF_3$, —$(CH_2)_n$—$CHF_2$, —$(CH_2)_n$—CN, —$(CH_2)_n$-cycloalkyl, —$(CH_2)_n$—O-lower alkyl, —$(CH_2)_n$—O-cycloalkyl or —$(CH_2)_n$—C(O)O-lower alkyl;

$R^2$ is hydrogen, lower alkyl, lower alkoxy, halogen, —C(O)-lower alkyl, —C(O)OH, —C(O)O-lower alkyl, —$NR^3R^4$ or —C(O)—$NR^3R^4$ and wherein $R^3$ and $R^4$ is hydrogen or lower alkyl;

X and X' are taken together to form —O—, —S—, —$CH_2$, —$OCH_2$—, as a bridge between the two rings or individually are two hydrogen atoms not capable of forming a bridge; and n signifies 0, 1, 2, 3 or 4;

or a pharmaceutically acceptable salt thereof.

2. A compound of formula IA in accordance with claim 1,

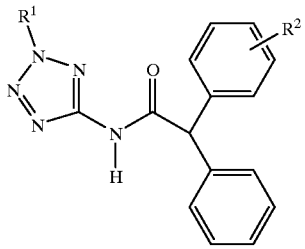

wherein $R^1$ and $R^2$ are as defined in claim 1.

3. The compound of claim 2 wherein $R^1$ is lower alkyl and $R^2$ is hydrogen.

4. The compound of claim 3 wherein the compound is N-(2-methyl-2H-tetrazol-5-yl)-2,2-diphenyl-acetamide.

5. The compound of claim 3 wherein the compound is N-(2-ethyl-2H-tetrazol-5-yl)-2,2-diphenyl-acetamide.

6. The compound of claim 3 wherein the compound is N-(2-isopropyl-2H-tetrazol-5-yl)-2,2-diphenyl-acetamide.

7. The compound of claim 3 wherein the compound is 2,2-diphenyl-N-(2-propyl-2H-tetrazol-5-yl)-acetamide.

8. The compound of claim 3 wherein the compound is N-(2-tert-butyl-2H-tetrazol-5-yl)-2,2-diphenyl-acetamide.

9. The compound of claim 2 wherein $R^1$ is —$(CH_2)_n$-$CF_3$, —$(CH_2)_n$—$CHF_2$ or —$(CH_2)_n$—CN and $R^2$ is hydrogen.

10. The compound of claim 9 wherein the compound is 2,2-diphenyl-N-[2-(2,2,2-trifluoro-ethyl)-2H-tetrazol-5-yl]-acetamide.

11. The compound of claim 9 wherein the compound is N-(2-difluoromethyl-2H-tetrazol-5-yl)-2,2-diphenyl-acetamide.

12. The compound of claim 9 wherein the compound is N-(2-cyanomethyl-2H-tetrazol-5-yl)-2,2-diphenyl-acetamide.

13. The compound of claim 2 wherein $R^1$ is —$(CH_2)_n$—C(O)O-lower alkyl and $R^2$ is hydrogen.

14. The compound of claim 13 wherein the compound is (5-diphenylacetylamino-tetrazol-2-yl)-acetic acid methyl ester.

15. The compound of claim 2 wherein $R^1$ is —$(CH_2)_n$-cycloalkyl and $R^2$ is hydrogen.

16. The compound of claim 15 wherein the compound is N-(2-cyclopropylmethyl-2H-tetrazol-5-yl)-2,2-diphenyl-acetamide.

17. The compound of claim 2 wherein $R^1$ is —$(CH_2)_n$—O-lower alkyl and $R^2$ is hydrogen.

18. The compound of claim 17 wherein the compound is N-(2-methoxymethyl-2H-tetrazol-5-yl)-2,2-diphenyl-acetamide.

19. A compound of formula IB in accordance with claim 1,

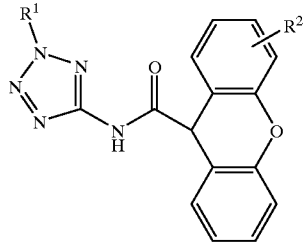

wherein $R^1$ and $R^2$ are as defined in claim 1.

20. The compound of claim 19 wherein $R^1$ is lower alkyl and $R^2$ is hydrogen.

21. The compound of claim 20 wherein the compound is 9H-xanthene-9-carboxylic acid (2-methyl-2H-tetrazol-5-yl)-amide.

22. The compound of claim 20 wherein the compound is 9H-xanthene-9-carboxylic acid (2-ethyl-2H-tetrazol-5-yl)-amide.

23. The compound of claim 20 wherein the compound is 9H-xanthene-9-carboxylic acid (2-isopropyl-2H-tetrazol-5-yl)-amide.

24. The compound of claim 20 wherein the compound is 9H-xanthene-9-carboxylic acid (2-propyl-2H-tetrazol-5-yl)-amide.

25. The compound of claim 20 wherein the compound is 9H-xanthene-9-carboxylic acid (2-tert-butyl-2H-tetrazol-5-yl)-amide.

26. The compound of claim 19 wherein $R^1$ is —$(CH_2)_n$-cycloalkyl and $R^2$ is hydrogen.

27. The compound of claim 26 wherein the compound is 9H-xanthene-9-carboxylic acid (2-cyclopropylmethyl-2H-tetrazol-5-yl)-amide.

28. The compound of claim 19 wherein $R^1$ is —$(CH_2)_n$—$CF_3$, —$(CH_2)_n$—$CHF_2$ or —$(CH_2)_n$—CN and $R^2$ is hydrogen.

29. The compound of claim 28 wherein the compound is 9H-xanthene-9-carboxylic acid [2-(2,2,2-trifluoro-ethyl)-2H-tetrazol-5-yl]-amide.

30. The compound of claim 28 wherein the compound is 9H-xanthene-9-carboxylic acid (2-difluoromethyl-2H-tetrazol-5-yl)-amide.

31. The compound of claim 28 wherein the compound is 9H-xanthene-9-carboxylic acid (2-cyanomethyl-2H-tetrazol-5-yl)-amide.

32. The compound of claim 19 wherein $R^1$ is —$CH_2$n—O-lower alkyl and $R^2$ is hydrogen.

33. The compound of claim 32 wherein the compound is 9H-xanthene-9-carboxylic acid (2-methoxymethyl-2H-tetrazol-5-yl)-amide.

34. The compound of claim 19 wherein $R^1$ is —$(CH_2)_n$—C(O)O-lower alkyl and $R^2$ is hydrogen.

35. The compound of claim 34 wherein the compound is {5-[(9H-xanthene-9-carbonyl)-amino]-tetrazol-2-yl}-acetic acid methyl ester.

36. The compound of claim 19 wherein $R^1$ is lower alkyl and $R^2$ is lower alkoxy.

37. The compound of claim 36 wherein the compound is (RS)-1-methoxy-9H-xanthene-9-carboxylic acid (2-ethyl-2H-tetrazol-5-yl)-amide.

38. The compound of claim 36 wherein the compound is (RS)-2-methoxy-9H-xanthene-9-carboxylic acid (2-ethyl-2H-tetrazol-5-yl)-amide.

39. The compound of claim 36 wherein the compound is (RS)-4-methoxy-9H-xanthene-9-carboxylic acid (2-ethyl-2H-tetrazol-5-yl)-amide.

40. A compound of formula IC in accordance with claim 1,

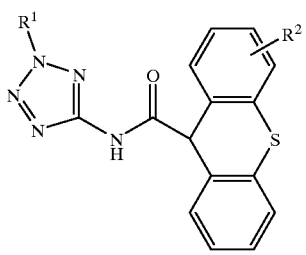

IC wherein $R^1$ and $R^2$ are as defined in claim 1.

41. The compound of claim 40 wherein the compound is 9H-thioxanthene-9-carboxylic acid (2-ethyl-2H-tetrazol-5-yl)-amide.

42. A compound of formula ID in accordance with claim 1,

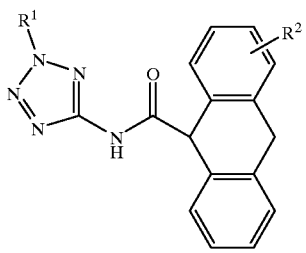

ID wherein $R^1$ and $R^2$ are as defined in claim 1.

43. The compound of claim 42 wherein the compound is 9,10-dihydro-anthracene-9-carboxylic acid (2-ethyl-2H-tetrazol-5-yl)-amide.

44. A compound of formula IE in accordance with claim 1,

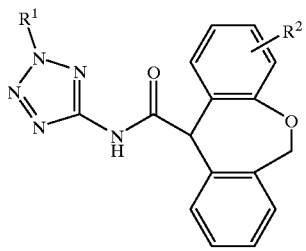

IE wherein $R^1$ and $R^2$ are as defined in claim 1.

45. The compound of claim 44 wherein the compound is (RS)-6,11-dihydro-dibenzo[b,e]oxepine-11-carboxylic acid (2-ethyl-2H-tetrazol-5-yl)-amide.

46. A medicament comprising an effective amount of the compound of claim 1 having the structure of formula I or a pharmaceutically acceptable salt thereof; and at least one pharmaceutically acceptable excipient.

47. A method of treatment of a patient comprising administering a sufficient quantity of the medicament in accordance with claim 46 for the control or prevention of acute and/or chronic neurological disorders to a patient in need of such treatment.

48. A process for the manufacture of the compounds of claim 1 having the structure of formula I or a pharmaceutically acceptable salt thereof, which process comprises reacting a compound of formula

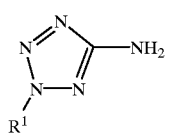

II with a compound of formula

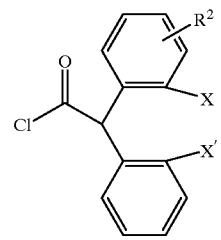

III to a compound of formula

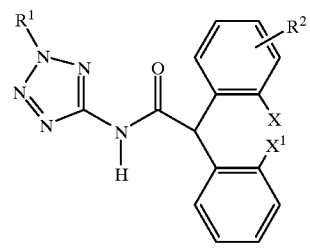

wherein the $R^1$, $R^2$, X and X' are as described in claim 1.

49. The process of claim 48 further comprising converting the compound of formula I into a pharmaceutically acceptable salt.

* * * * *